(12) United States Patent
Lee et al.

(10) Patent No.: US 9,146,605 B2
(45) Date of Patent: Sep. 29, 2015

(54) ULTRA LOW POWER ACTIGRAPHY BASED ON DYNAMIC THRESHOLD

(71) Applicants: Yong Jin Lee, Palo Alto, CA (US); Eddy Hui, Kowloon (HK); Kaiping Chen, San Jose, CA (US)

(72) Inventors: Yong Jin Lee, Palo Alto, CA (US); Eddy Hui, Kowloon (HK); Kaiping Chen, San Jose, CA (US)

(73) Assignee: SALUTRON, INC., Fremont, CA (US)

( * ) Notice: Subject to any disclaimer, the term of this patent is extended or adjusted under 35 U.S.C. 154(b) by 203 days.

(21) Appl. No.: 13/755,778

(22) Filed: Jan. 31, 2013

(65) Prior Publication Data

US 2014/0215246 A1    Jul. 31, 2014

(51) Int. Cl.
| G06F 1/00 | (2006.01) |
| G06F 1/32 | (2006.01) |
| A61B 5/0205 | (2006.01) |
| A61B 5/024 | (2006.01) |
| A61B 5/11 | (2006.01) |
| A61B 5/00 | (2006.01) |
| G04G 19/12 | (2006.01) |
| G06F 3/03 | (2006.01) |

(Continued)

(52) U.S. Cl.
CPC .......... *G06F 1/3206* (2013.01); *A61B 5/02055* (2013.01); *A61B 5/02438* (2013.01); *A61B 5/1118* (2013.01); *A61B 5/681* (2013.01); *G04C 10/00* (2013.01); *G04G 19/12* (2013.01); *G04G 21/025* (2013.01); *G06F 3/03* (2013.01); *A61B 2562/0219* (2013.01)

(58) Field of Classification Search
USPC ........ 342/162, 357.25, 357.57; 702/141, 193; 600/549, 595; 713/300, 320, 323
See application file for complete search history.

(56) References Cited

U.S. PATENT DOCUMENTS

| 5,343,411 A | * | 8/1994 | Olsson .......................... 702/141 |
| 5,610,337 A | * | 3/1997 | Nelson ............................. 73/651 |
| 7,216,053 B2 | | 5/2007 | Rakkola et al. |

(Continued)

FOREIGN PATENT DOCUMENTS

| CN | 101518442 B | 4/2011 |
| EP | 1752841 A1 | 2/2007 |

(Continued)

OTHER PUBLICATIONS

Malinowski, Mateusz, et al., "CargoNet: A Low-Cost MicroPower Sensor Node Exploiting Quasi-Passive Wakeup for Adaptive Asynchronous Monitoring of Exceptional Events," SenSys ;07, Nov. 6-9, 2007, 15 pages.

(Continued)

*Primary Examiner* — Zahid Choudhury
(74) *Attorney, Agent, or Firm* — Vierra Magen Marcus LLP (57) ABSTRACT

A processor for an activity monitor for a user has a reduced power mode in which it does not process data samples from an accelerometer. A wake up circuit or logic evaluates an output from the accelerometer and determines whether the output exceeds a threshold, indicating a threshold amount of activity of the user. If the threshold is exceeded, the wake up circuit or logic causes the processor to enter an active mode. The processor evaluates samples of the accelerometer in an evaluation period and decides whether to continue in the active mode or return to the reduced power mode. If the user is deemed to be sufficiently active, the processor continues in the active mode. In another aspect, the threshold can be set based on an activity level of the user before the reduced power mode or sensor data such as ambient light level or skin temperature.

24 Claims, 7 Drawing Sheets

(51) Int. Cl.
*G04C 10/00* (2006.01)
*G04G 21/02* (2010.01)

(56) References Cited

U.S. PATENT DOCUMENTS

| | | |
|---|---|---|
| 7,559,899 B2 | 7/2009 | Lo et al. |
| 7,652,609 B2 | 1/2010 | Kim et al. |
| 8,041,328 B2 | 10/2011 | Orr et al. |
| 8,239,160 B2 | 8/2012 | Lee et al. |
| 8,328,718 B2 | 12/2012 | Tran |
| 2004/0172167 A1 | 9/2004 | Pasolini et al. |
| 2008/0016961 A1 | 1/2008 | Dwyer et al. |
| 2010/0063365 A1 | 3/2010 | Pisani et al. |
| 2010/0100004 A1* | 4/2010 | van Someren ............ 600/549 |
| 2011/0152637 A1 | 6/2011 | Kateraas et al. |
| 2012/0197095 A1 | 8/2012 | Sholder |
| 2012/0274508 A1 | 11/2012 | Brown et al. |
| 2013/0158686 A1* | 6/2013 | Zhang et al. .............. 700/91 |

FOREIGN PATENT DOCUMENTS

JP      S60108787 A     6/1985

WO      WO 2009/140360 A1    11/2009

OTHER PUBLICATIONS

"Micropower, 3-Axis, +−2 g/+−4 g/+−8 g Digital Output MEMS Accelerometer," Analog Devices, Sep. 2012, 44 pages.

Tuck, Kimberly, "Auto-Wake/Sleep Using the MMA8451, 2, 3Q," Freescale Semiconductor, Inc., Document No. AN4074, Rev. 1, Mar. 2012, 10 pages.

Cohn, Gabe, et al., "An Ultra-Low-Power Human Body Motion Sensor Using Static Electric Field Sensing," UbiComp' 12, Sep. 5-8, 2012, 4 pages.

English Abstract of European Publication No. EP1752841 published Feb. 14, 2007.

English Abstract of Chinese Publication No. CN101518442 published Sep. 2, 2009.

English Abstract of Japanese Publication No. JPS60108787 published Jun. 14, 1985.

International Search Report & The Written Opinion of the International Searching Authority dated Apr. 24, 2014, International Application No. PCT/US2014/013680.

* cited by examiner

ULTRA LOW POWER ACTIGRAPHY BASED ON DYNAMIC THRESHOLD

BACKGROUND

Activity monitors or actigraphs have become popular as a tool for promoting exercise and a healthy lifestyle. An activity monitor can include an accelerometer which can measure motions such as steps taken while walking or running, and estimate an amount of calories used. Moreover, user-specific information such as age, gender, height and weight can be used to tailor the estimate to the user. Such monitors can be worn on the wrist, belt or arm, for instance, or carried in the pocket. The monitor can be worn during an intended workout period or as a general, all day, free living monitor, where the user may perform specific exercises at some times while going about their daily activities at other times, e.g., including sitting, standing and sleeping.

An activity monitor can include a heart rate monitor. Heart rate monitors are also used to monitor individuals, typically during an exercise session in which the user tries to maintain a target heart rate. Some ECG-based monitors are worn on a chest strap, where the electrodes of the monitor are constantly in contact with the body and can therefore continuously determine heart rate. Heart rate data can be transmitted from the chest strap to a display such as on a wrist worn device for easy viewing by the user. Other monitors are wrist-worn, for example, and only determine the heart rate on demand, when the user touches electrodes on the monitor or provides another manual control input. Optical sensors can also be used to determine heart rate.

SUMMARY

As described herein, an activity monitor is provided in which a processor has a reduced power mode. This leads to a longer battery life, which is useful especially for non-rechargeable monitors. Techniques for transitioning from the reduced power mode to an active mode are provided which account for the activity level of the user. As a result, the reduced power mode can be used when the user is essentially inactive, even if a significant acceleration output is detected. Power savings can thereby be realized.

In one approach, an activity monitor includes an accelerometer adapted to be worn by a user, a wake up circuit which determines whether an output from the accelerometer exceeds a threshold and a processor. The processor is in communication with the accelerometer and the circuit. Further, the processor is adapted to process samples from the accelerometer in an active mode of the processor but not in a reduced power mode of the processor. The circuit causes the processor to enter the active mode from the reduced power mode when the output exceeds the threshold. The processor, upon entering the active mode, evaluates samples from the accelerometer in an evaluation period, and based on the evaluation, determines an activity level of the user, and based on the activity level, determines whether to remain in the active mode or to transition back to the reduced power mode.

In another approach, an activity monitor includes an accelerometer adapted to be worn by a user, and a processor. The processor includes wake up logic and activity analysis logic. The wake up logic determines whether an output from the accelerometer exceeds a threshold and a processor. Further, the activity analysis logic is adapted to process samples from the accelerometer in an active mode of the processor but not in a reduced power mode of the processor. The wake up logic causes the processor to enter the active mode from the reduced power mode when the output exceeds the threshold. The processor, upon entering the active mode, uses the activity analysis logic to evaluate samples from the accelerometer in an evaluation period, and based on the evaluation, determine an activity level of the user, and based on the activity level, determine whether to remain in the active mode or to transition back to the reduced power mode.

In another aspect, the threshold can be set dynamically and adaptively based on characteristics of the user, time of day, a history of the accelerometer signal as well as inputs from other sensors such as an ambient light sensor and a skin temperature sensor.

This summary is provided to introduce a selection of concepts in a simplified form that are further described below in the description. This summary is not intended to identify key features or essential features of the claimed subject matter, nor is it intended to be used to limit the scope of the claimed subject matter.

BRIEF DESCRIPTION OF THE DRAWINGS

In the drawings, like-numbered elements correspond to one another.

DETAILED DESCRIPTION

An activity monitor is provided for detecting an amount of energy, e.g., calories, burned by a user over a period of time, where the monitor includes power saving features. Specifically, to conserve power, the accelerometer is put into a less active, reduced power state until a certain threshold level of user activity is detected. When the threshold level of user activity is detected, a short section of the waveform is analyzed to determine whether the accelerometer signal should continue to be analyzed. The threshold for waking up the accelerometer can be a function of the history of the accelerometer signal as well as inputs from other sensors such as an ambient light sensor and skin temperature sensor.

Figures 1A, 1B:
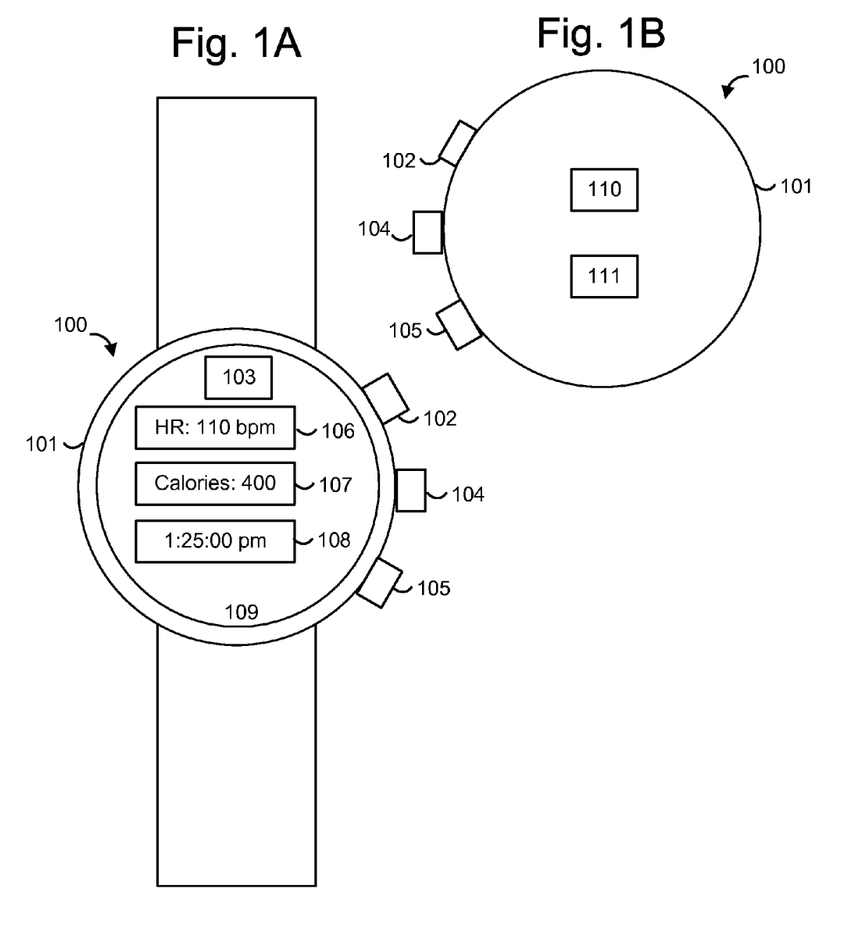
FIG. 1A depicts a front view of an example activity monitor.
FIG. 1B depicts a rear view of the activity monitor of FIG. 1A.

FIG. 1A depicts a front view of an example activity monitor. The activity monitor 100 can be a wristwatch type device comprising a watch face and a strap for wearing around the wrist in this example, but other implementations are possible. For example, such monitors can be worn on the belt, head, chest, arm or carried in the pocket. A monitor could also include multiple components which are attached to different parts of the body. For example, the different components can include accelerometers which are attached to different parts of the body, e.g., the arm and leg, to gain a more complete understanding of the user's activity, including posture. The activity monitor 100 includes a case 101, a crown 104, a mode select button 105 and a heart rate request button 102. A display device 109 includes an ambient light sensor 103, a region 106 which depicts a heart rate (HR) (e.g., 110 beats per minutes or bpm), a region 107 which depicts an amount of calories (e.g., 400 calories) consumed in a monitoring session, and a region 108 which depicts a time of day (e.g., 1:25:00 pm). The mode select button 105 may allow the user to activate different operational modes and to input user-specific information such as age, gender, height, weight or body mass index.

The activity monitor can include an on-demand heart rate monitor which determines the heart rate in response to a specific manual user action. For example, the heart rate can be determined when the user touches the heart rate request button 102. In one approach, the heart rate request button 102 is an electrode which is used to complete an ECG circuit to detect the heart rate. In this case, an additional electrode can be provided on the back of the activity monitor which contacts the user's skin. Ultrasonic and optical based monitors can also be used. These types of monitors are popular since they do not require an electrode-carrying chest strap. They allow the user to check his heart rate from time to time rather than continuously. In another approach, the heart rate is continuously measured such as by a chest strap which transmits the heart rate wirelessly for display on the display device 109.

FIG. 1B depicts a rear view of the activity monitor of FIG. 1A. In this example, an optical component 110 emits light into the user's body and detects reflections, to determine the heart rate. A skin temperature sensor 111 is also provided. Skin temperature can be used to determine activity and calories burned, for instance.

Figure 1C:
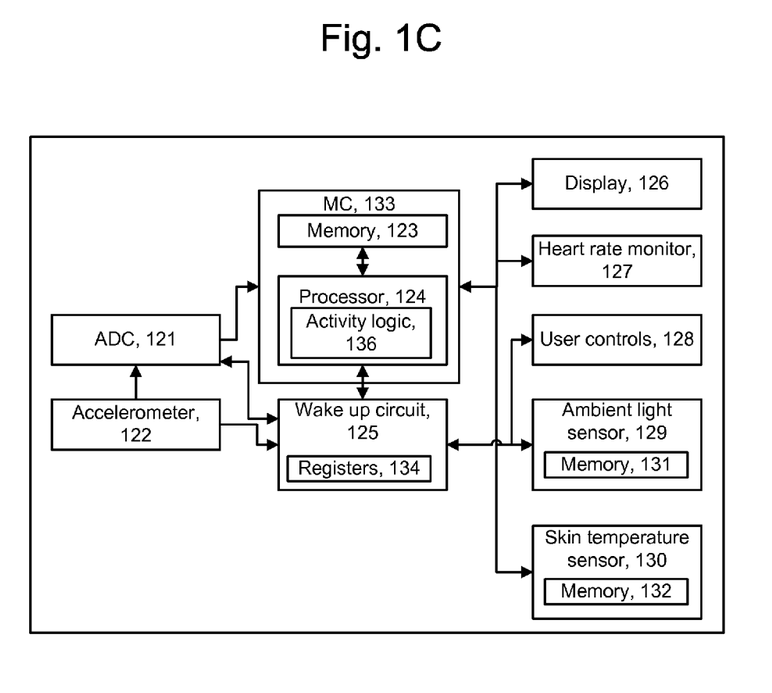
FIG. 1C depicts an example block diagram of the activity monitor of FIG. 1A.

FIG. 1C depicts an example block diagram of the activity monitor of FIG. 1A. A micro-controller (microprocessor controller, MC) 133 includes a processor 124 having activity analysis logic 136. The processor communicates with a memory 123. The micro-controller communicates with a number of components including an analog-to-digital converter (ADC) 121, a wake up circuit 125 (e.g., a hardware circuit) including registers 134, a display device 126, a heart rate monitor 127, user controls 128, an ambient light sensor 129 including a memory 131 and a skin temperature sensor 130 including a memory 132. Also provided is an accelerometer 122, such as a three-axis accelerometer. In this approach, the accelerometer provides an analog output signal representing acceleration in one or more directions. The analog outputs are digitized by the ADC 121 and digital samples are provided to the processor 124. The ADC could be part of the MC/processor. The wake up circuit also receives the analog output signal from the accelerometer. In another approach, the wake up circuit receives and processes digital samples of the accelerometer. The ambient light sensor may include, e.g., a light-dependent resistor or a photodiode. The skin temperature sensor may include, e.g., a thermistor, a type of resistor whose resistance varies with temperature.

In one approach, a sensor has intelligence to provide an indication as to whether the active mode should be set. The sensor can thus indicate to the processor that the active mode should continue. The processor decides whether to continue the active mode based on this input, the user activity and possibly other factors. The sensors can compare the sensed data to one or more threshold values stored in a local memory, e.g., using memory 131 or 132. The threshold can be adaptively determined. For example, it can be generated based on a history of the acquired signal. Software may collect, e.g., three seconds of data from the accelerometer in order to generate a threshold for arbitration. For the light sensor, an amount of light in lux can be measured and compared to a threshold lux value. For the skin temperature sensor, a temperature in degrees C. or F. be measured and compared to a threshold value. Moreover, the software may determine a rate of changes of a sensed value over a short period of time such as a few seconds. The rate of change data is stored in a buffer of the processor and analyzed similar to the way the user activity is analyzed, e.g., to determine whether to remain in the active mode or for other reasons. Note that some sensors may require a certain time interval to generate and provide a signal to the processor. In such a case, an interrupt signal from the sensor to the processor can be used to inform the processor that the data is ready and should be obtained by the processor.

The diagram is meant to provide a high level understanding of the activity monitor. Specific implementations can take many forms. For example, accelerometer signals can be subject to analog signal processing, analog to digital conversion, time domain processing, conversion to the frequency domain such using a Fast Fourier Transform and frequency domain processing. Heart rate signals can be similarly processed.

The MC may be in communication with each of the other components and transmit signals to them and/or receive signals from them. The memory 123 can store code which is executed by the processor to perform the functionality described herein. The memory is an example of a computer-readable storage apparatus having computer-readable software embodied thereon for programming a processor to perform a method. For example, non-volatile memory can be used. Volatile memory such as a working memory of the processor can also be used. The display device 126 can represent circuitry used to provide the display device 109 of FIG. 1A, for instance. The heart rate monitor 127 determines a current heart rate of a user either on demand or continuously. The user controls 128 can include the mode select button 105 of FIG. 1A, for instance and associated components. The accelerometer 122 provides acceleration readings at a prescribed rate such as multiple times per second.

The registers could be used to store adjustable parameters such as a wake up threshold (Th) and sampling rate.

Figure 1D:
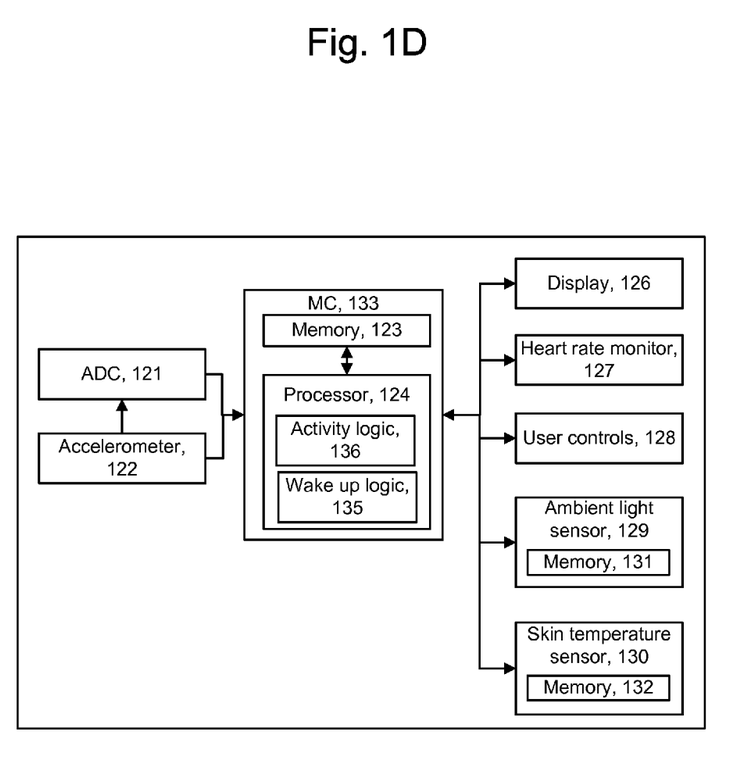
FIG. 1D depicts another example block diagram of the activity monitor of FIG. 1A. In this approach, wake up logic (software) 135 is provided as part of the processor.

FIG. 1D depicts another example block diagram of the activity monitor of FIG. 1A. In this approach, wake up logic (software) 135 is provided as part of the processor.

Figure 2A:
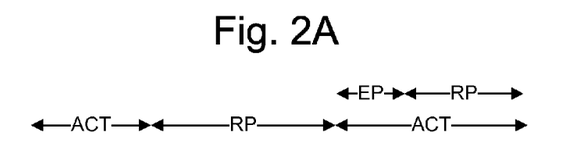
FIG. 2A depicts transitions between active (ACT) and reduced power (RP) modes of a processor of the activity monitor.

FIG. 2A depicts transitions between active (ACT) and reduced power (RP) modes of a processor of the activity monitor. The processor can assume an active mode from time to time in which it processes samples from the accelerometer.

In this case, a relatively high sampling rate can be used, e.g., hundreds of times per second, and the amplitude of the samples can be multi-bit values which allow the acceleration amplitude to be determined with high accuracy. The acceleration samples can be used to determine an activity level of the user and, in some cases, a type of the activity. Based on this, calorie consumption and other metrics can be calculated. In the active mode, power is consumed in transferring the samples from the accelerometer to the processor and by the processor and associated memory in processing and storing the samples.

The processor can assume a reduced power mode when it is not in the active mode. The processor could alternatively be in an off mode when it is not in the active mode. In the reduced power mode, in the approach of FIG. 1C, the processor does not process samples from the accelerometer. Power is saved by not transferring the samples from the accelerometer to the processor and by the processor and associated memory in not processing and storing the samples. Instead, the wake up circuit compares an output from the accelerometer to a threshold and decides whether to trigger the active mode in the processor including the activity analysis logic. The wake up circuit can use a relatively low sampling rate. In the reduced power mode, in the approach of FIG. 1D, the processor processes samples from the accelerometer at a relatively low sampling rate using the wake up logic. Power is saved by not processing the samples at a high rate and by not using the activity analysis logic. The processor compares an output from the accelerometer to a threshold, e.g., using a relatively low sampling rate. The processor compares an output from the accelerometer to a threshold and decides whether to trigger the active mode in the processor including the activity analysis logic. The reduced power mode Moreover, a decision can be made to remain in the active mode based on various criteria as described herein. In one approach, an evaluation period (EP) is used as an initial part of the active mode in which the processor determines whether the user is sufficiently active to continue to remain in the active mode. Otherwise, the processor returns to the reduced power mode.

Figure 2B:
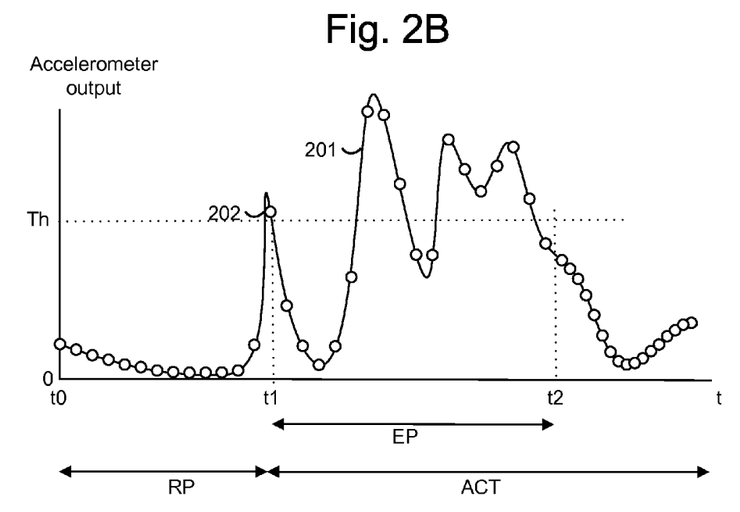
FIG. 2B depicts example accelerometer readings during active (ACT) and reduced power (RP) modes of a processor of the activity monitor.

FIG. 2B depicts example accelerometer readings during active (ACT) and reduced power (RP) modes of a processor of the activity monitor. In this example, the continuous line 201 represents an output analog signal from the accelerometer. An accelerometer has the ability to measure acceleration in one, two or three directions, such as along the x, y and z axes of a Cartesian coordinate system. The magnitude of acceleration can be determined as well. A movement of a user is represented by acceleration readings, e.g., along the x, y and z axes. In one approach, each movement results in an activity count. Generally, the level of activity of a user over time can be determined based on the acceleration readings. For example, amplitude, frequency and zero-crossings of the acceleration can be used to determine a level of activity. Higher amplitudes, frequencies and zero-crossings are associated with a higher activity level.

In the example provided, time extends on the horizontal axis and amplitude is on the vertical axis. The amplitude could represent a component (Ax, Ay, Az) along one of the x, y and z axes of an amplitude vector, or the amplitude could represent the magnitude of an amplitude vector, e.g., the square root of $Ax^2+Ay^2+Az^3$. The amplitudes are expressed by absolute values in this example. Each circle represents a reading from the line 201. A reduced power mode extends from t0-t1 and an active mode extends from t1, including an evaluation period from t1-t2. In one approach, the processor in the active mode uses a higher sampling rate of the acceleration data than a sampling rate of the wake up circuit or logic.

In some cases, the type of exercise that a user is performing can be detected based on characteristics of the accelerometer readings. For example, a training process may be performed in which the user performs specified exercises and the resulting accelerometer readings are recorded. Accelerometer readings from a subsequent exercise period can be compared to the recorded accelerometer readings (signatures) to identify the exercise being performed, as well as a pace of the exercise based on the frequency of movement. For example, it may be determined that a user is running at 3 miles per hour. The type of exercise which is performed and the pace of the exercise can further be correlated with a rate of calories burned by the user based on scientific studies which have been published. The rate of calories burned can be tailored to a particular user based on factors such as age, gender, height and weight. This information can all be encompassed within control logic of the processor using appropriate formulas and tables.

As described further below, the evaluation period can be triggered by the wake up circuit or logic detecting one or more accelerometer readings (e.g., reading 202) above Th, such as at time t1. The wake up circuit or logic can be relatively simple and consume relatively little power as it can simply compare the output to the threshold to determine which is greater. The wake up circuit or logic can store an initial value of the threshold and updates to the threshold.

Figure 3A:
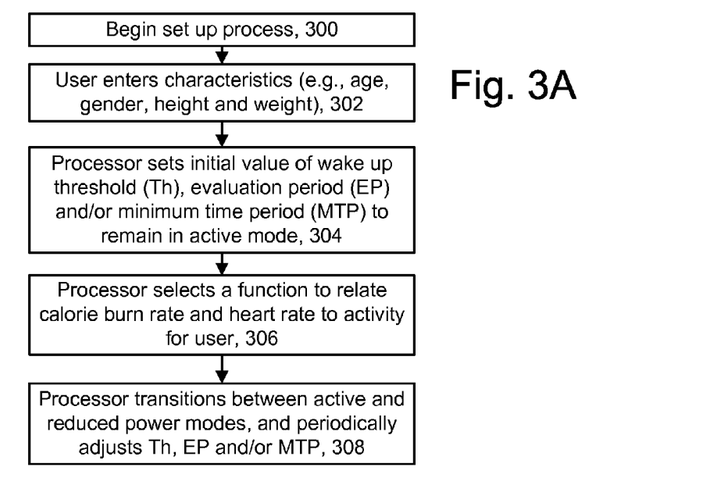
FIG. 3A depicts a setup process for the activity monitor of FIG. 1A.

FIG. 3A depicts a setup process for the activity monitor of FIG. 1A. At step 300, the setup process begins. For example, the user may use the mode select button 105 to enter information such as by scrolling through menus on the display device. At step 302, the user enters personal characteristics (e.g., age, gender, height, weight and/or body mass index). In another approach, the activity monitor can communicate with a host computing device which provides a user interface to obtain the personal characteristics. At step 304, the processor sets an initial value of the wake up threshold (e.g., an initial value of Th in FIG. 2B), an initial value of the evaluation period (EP) and an initial value of a minimum time period (MTP) to remain in the active mode (either from a start of the active mode or from an end of the EP).

At step 306, the processor selects a function to relate calorie burn rate and heart rate to activity for the user. For example, see FIG. 3F which depicts a relationship between activity type and calorie burn rate. In a simplified example, different activities, e.g., Activity 1 or 2, and different intensities, e.g., 1, 2 and 3 can be associated with calorie burn rates (CBR). Calorie burn rates can be provided for repetitive activities such as certain exercises and non-repetitive activities such as sleeping and sitting. FIG. 3G depicts a relationship between calorie burn rate and heart rate. At step 308, the processor transitions between the active and reduced power modes, and can periodically adjust Th, EP and/or MTP, as described further below.

Figure 3B:
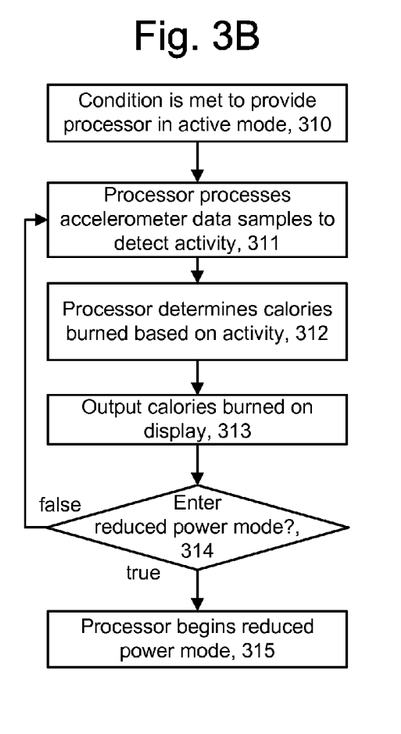
FIG. 3B depicts a process performed by the processor 124 of FIG. 1C in the active mode in accordance with step 308 of FIG. 3A.

FIG. 3B depicts a process performed by the processor 124 of FIG. 1C in the active mode in accordance with step 308 of FIG. 3A. The process begins at step 310 where a condition has been met to provide the processor in an active mode, such as described in connection with FIG. 3E or upon initial power up. At step 311, the processor processes the accelerometer data samples to detect activity of the user. For example, this can include processing the samples after t1 in FIG. 2B. At step 312, the processor determines calories burned based on the activity such as by reference to FIG. 3F. Step 313 involves outputting the calories burned on the display device. Generally, data regarding calorie expenditures can be viewed on the display device and/or uploaded to an online service for viewing and further analysis. Decision step 314 determines if a condition has been met to enter the reduced power mode, such as described in connection with FIG. 3C. If decision step 314 is true, the processor begins the reduced power mode at step 315. If decision step 314 is false, step 311 is repeated.

Figure 3C:
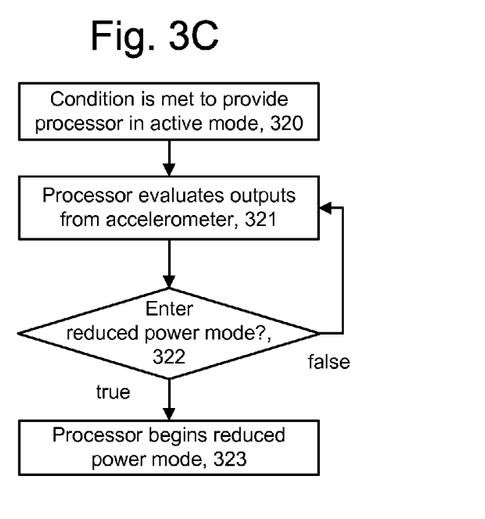
FIG. 3C depicts a process to determine when to enter the reduced power mode in accordance with step 314 of FIG. 3B.

FIG. 3C depicts a process to determine when to enter the reduced power mode in accordance with step 314 of FIG. 3B. The process begins at step 320 where a condition has been met to provide the processor in an active mode. At step 321, the processor evaluates outputs from accelerometer. For example, processor can decide to enter a reduced power mode after determining that no significant user activity has been detected for a specific period of time, such as several seconds or minutes. The processor can evaluate the full resolution, high sampling rate accelerometer readings to make this decision. Alternatively, the wake up circuit or logic can evaluate the analog accelerometer signals, or the digital samples, to make this decision. Decision step 322 determines whether to enter the reduced power mode. If decision step 322 is true, the processor begins the reduced power mode at step 323. If decision step 322 is false, step 321 is repeated.

Figure 3D:
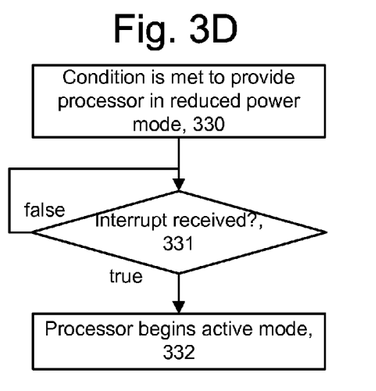
FIG. 3D depicts a process performed by the processor 124 of FIG. 1C in the reduced power mode in accordance with step 308 of FIG. 3A.

FIG. 3D depicts a process performed by the processor 124 of FIG. 1C in the reduced power mode in accordance with step 308 of FIG. 3A. The process begins at step 330 where a condition has been met to provide the processor in a reduced power mode. Decision step 331 determines whether an interrupt request has been received by the processor. Generally, an interrupt request can be a signal which is sent to the processor by hardware or software. It indicates an event has occurred that requires immediate attention. The current code or thread that the processor is executing, e.g., a thread for the reduced power mode, is interrupted, beginning the active mode. If decision step 331 is true, the processor begins the active mode at step 332. If decision step 331 is false, it waits until an interrupt request has been received.

Figure 3E:
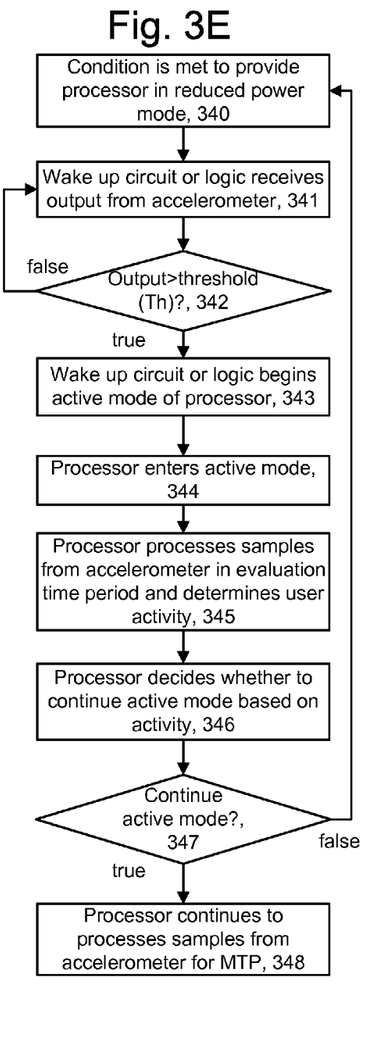
FIG. 3E depicts a process performed in the active mode in accordance with step 308 of FIG. 3A.

FIG. 3E depicts a process performed in the active mode in accordance with step 308 of FIG. 3A. The active or reduced power status of the processor can be known to the wake up circuit or logic. The process begins at step 340 where a condition has been met to provide the processor in a reduced power mode. At step 341, the wake up circuit or logic receives an output from the accelerometer. For example, the output can be an analog signal, or digital samples from an ADC. The wake up circuit or logic can process outputs from the accelerometer at a specified rate. In one approach, it is less than a rate of the processor. Further, the sampling rate of the wake up circuit or logic can be adjustable.

Decision step 342 determines whether the output>threshold (Th) (see FIG. 2B). In one approach, the wake up circuit or logic only determines if an accelerometer reading is above or below a threshold level while the processor determines the precise acceleration level with multiple bits of resolution. The wake up circuit or logic can thus be relatively simple and consume a small amount of power since it does not perform extensive processing. Further, the comparison can involve one threshold level for one axis of acceleration or a separate threshold level for each axis of acceleration (e.g., x, y and z).

Figure 4:
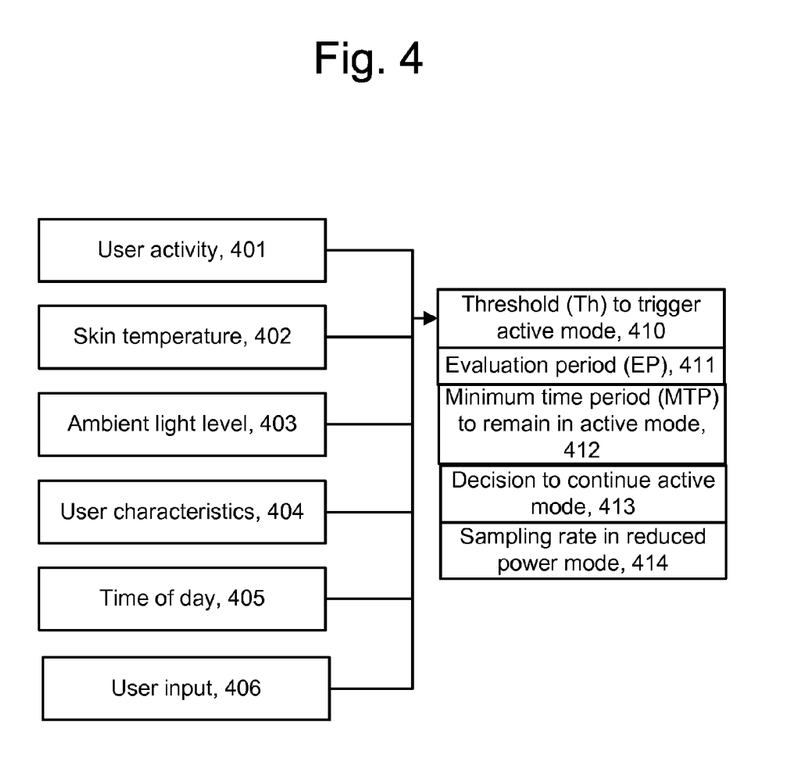
FIG. 4 depicts factors which can be used in adjusting variables such as the threshold (Th) to trigger the active mode (block 410), a duration of the evaluation period (EP) (block 411) a minimum time period (MTP) to remain in active mode (block 412) in accordance with step 308 of FIG. 3A, as well as in deciding whether to remain in the active mode in accordance with step 346 of FIG. 3E (block 413) and a sample rate in the reduced power mode (block 414).

If decision step 342 is true, the wake up circuit or logic begins the active mode of the processor at step 343. For example, an interrupt request can be provided to the processor to begin the active mode. Or, the wake up logic can call a method of the active mode. If decision step 342 is false, step 341 is repeated. The processor enters the active mode at step 344. At step 345, the processor, e.g., using the activity analysis logic, processes samples from the accelerometer in the EP and determines a level of the user activity during the EP. At step 346, the processor decides whether to continue the active mode based on the level of activity. A number of factors such as depicted in FIG. 4 can be used to make this decision. For example, one factor is whether the there is a sufficient amount of activity to justify using the active mode. For example, the user may be sleeping and make a brief motion such as moving the arm which results in the threshold being exceeded. However, the user continues to sleep quietly after that. In this case, continuing the active mode is not justified. On the other hand, the user may stand up and begin running, in which case continuing the active mode is justified.

In one approach, higher amplitudes, frequencies and zero-crossings are associated with a higher activity level. Also, the processor can determine the number of activity counts, where more counts indicate more activity. Another approach determines a maximum frequency of the readings in the EP. The activity level can therefore be quantified and compared to an activity threshold. The active mode can be continued for at least the MTP if this number exceeds a threshold number. The EP could be a few seconds, for example. The EP could be a fixed, predetermined period.

In another approach, the evaluation determines a pattern in the acceleration readings and determines a type of activity of the user. A decision to continue the active mode can be based on the type of activity. For example, the active mode can be continued if the activity is a certain type of exercise. Combinations of factors can be used as well.

In another approach, the evaluation uses sensor data such as ambient light level. For example, if the ambient light level indicates it is night time, it may be concluded that the user is likely to be inactive, which is an indication that the reduced power mode should be used. If the ambient light level indicates it is day light, it may be concluded that the user is likely to be active, which is an indication that the active mode should be used.

In another approach, the evaluation uses sensor data such as skin temperature. For example, a low skin temperature may indicate the user is likely to be inactive, which is an indication that the reduced power mode should be used.

In another approach, the evaluation uses the time of day and/or day of week to determine whether it is likely that the user will be active.

Decision step 347 determines whether a decision has been made by the wake up circuit or logic to enter the active mode. If decision step 347 is true, the processor continues to process samples from the accelerometer for at least the MTP, at step 348. If decision step 347 is false, step 340 is reached and the processor returns to the reduced power mode. The MTP prevents the processor from returning to the reduced power mode too soon. For example, the user may be active during the EP and then become inactive. If the MTP was not used, the processor could return to the reduced power mode without considering that the user is likely to become active again. Moreover, the MTP can be adjusted so that it is higher when the user has had a relatively high level of activity during the EP or at earlier times. Use of the MTP is optional.

Figure 3F:
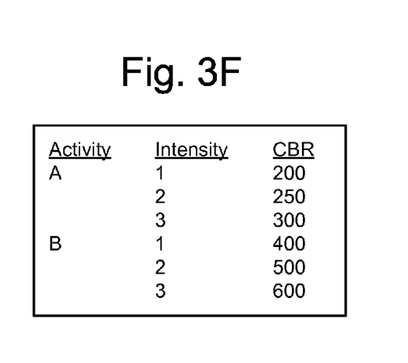
FIG. 3F depicts a relationship between activity type and calorie burn rate in accordance with step 312 of FIG. 3B.
Figure 3G:
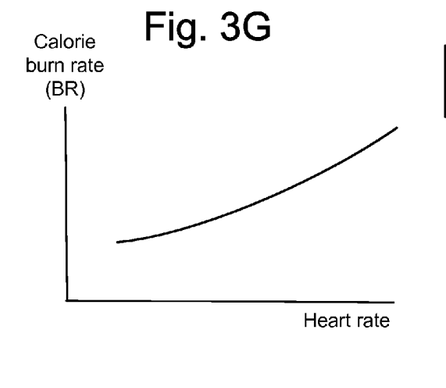
FIG. 3G depicts a relationship between heart rate and calorie burn rate (CBR) in accordance with step 306 of FIG. 3A.

FIG. 3F depicts a relationship between activity type and calorie burn rate (CBR) in accordance with step 312 of FIG. 3B. In a simplified example, different activities, e.g., Activity 1 or 2, and different intensities, e.g., 1, 2 and 3 can be associated with calorie burn rates (CBR). Calorie burn rates can be provided for repetitive activities such as certain exercises and non-repetitive activities such as sleeping and sitting.

FIG. 3G depicts a relationship between heart rate and calorie burn rate (CBR) in accordance with step 306 of FIG. 3A.

FIG. 4 depicts factors which can be used in adjusting variables such as the threshold (Th) to trigger the active mode (block 410), a duration of the evaluation period (EP) (block 411), a minimum time period (MTP) to remain in active mode (block 412) in accordance with step 308 of FIG. 3A, as well as in deciding whether to remain in the active mode in accordance with step 346 of FIG. 3E, and a sample rate in the reduced power mode (block 414). Various factors can be used. Generally, if the factor indicates the user has recently been relatively active, it is likely that the user will continue to be active. In this case, the variable can be adjusted to make entering the active mode easier when the next reduced power mode is reached. The active mode is thus favored. On the other hand, if the factor indicates the user has recently been relatively inactive, it is likely that the user will continue to be inactive and, the variable can be adjusted to make entering the active mode harder when the next reduced power mode is reached. The reduced power mode is thus favored. A lower Th value makes entering the active mode easier.

Any number of threshold levels can be used. The processor can configure parameters of the wake up circuit or logic with this information. The threshold can be adjustable The minimum time to remain in the active mode can be made longer when the user is relatively more active. The minimum time period ensures that the processor remains in the active mode for a certain time period, e.g., several seconds or minutes due to the likelihood of significant and imminent user activity.

Block 401 indicates that a user activity level can be a factor. For example, if the user has been generally active over several minutes or hours, it may be desirable to make entering the active mode easier. The previous or historical activity level can be based, e.g., on accelerations of the user or based on calorie consumption as a proxy for activity.

Block 402 indicates that skin temperature can be a factor. For example, a relatively high or increasing skin temperature over the past few minutes may indicate activity. On the other hand, a relatively low or decreasing skin temperature over the past few minutes may indicate inactivity, such as sleeping or resting.

Block 403 indicates that ambient light can be a factor. For example, if there is low light, this can indicate that it is night time or the user is indoors over the past few minutes, such that the user is less likely to be active. If there is bright light, this can indicate that it is day time or the user is outdoors over the past few minutes, such that the user is more likely to be active.

Block 404 indicates that user characteristics can be a factor. For example, for a person with limited mobility due to infirmity or excessive weight, it may be desirable to make entering the active mode easier.

Block 405 indicates that time of day can be a factor. For example, if it is night time, the user is less likely to be active. If it is day time, the user is more likely to be active. Or, specific information regarding the user's activity over time can be used to determine whether activity is more or less likely. For instance, a person may have unusual sleeping hours and this can be considered in determining whether activity is likely.

Block 406 indicates that user input can be a factor. For example, the user may set the wake up threshold to be lower or higher based on a preferred sensitivity of the activity monitor.

These factors can be evaluated periodically to determine whether an adjustment is indicated.

The duration of the evaluation period can be set based on factors which indicate that a shorter or longer EP is appropriate. For example, it may be harder to obtain an accurate determination of activity level for some users or under some conditions, in which case a longer EP can be used. Some users may be relatively slow moving due to overweightness or infirmity and it may take longer to evaluate their activity level.

The current heart rate or historical heart rate data could also be a factor.

The sampling rate could be lower when it is less likely that the user will be active.

Further, in the context of determining calorie consumption, if the user is less likely to be active, the calories consumed by occasional movements such as gesturing while talking in a seated position are not likely to be significant. Thus, it is an acceptable tradeoff to stay in the reduced power mode to save power by making it harder to enter the active mode. The penalty for missing the low calorie burning activity is low. The basal metabolic rate will dominate the calorie consumption metric.

On the other hand, if the user is more likely to be active, entering the active mode can be made easier to provide the processor in the active mode to detect activity which is likely to result in significant calorie consumption. The penalty for missing the high calorie burning activity is high. The exercise component becomes important in the calorie consumption metric.

Generally, the activity monitor can determine what the user is doing, e.g., whether he or she is sleeping, awake, exercising and so forth and make an intelligent decision of whether the active mode should be used to gather relevant activity data from the user or to continue a power saving, reduced power mode. This monitoring can occur in the context of an all-day activity monitor.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. An activity monitor, comprising:
an accelerometer adapted to be worn by a user and outputting an activity signal indicative of an activity level of the user;
a circuit in communication with the accelerometer and determining whether the activity signal output from the accelerometer exceeds a threshold; and
a processor configured to be in communication with the accelerometer and the circuit,
the processor is adapted to process data samples from the accelerometer in an active mode of the processor, and otherwise reduce power consumption of the activity monitor by not transferring the data samples from the accelerometer to the processor,
the circuit triggering the processor to enter the active mode, for a minimum period of time, from a reduced power mode when the activity signal output exceeds the threshold, and the minimum period of time is adjustable based on a determination that the user will remain active within the minimum period of time,
the processor, upon entering the active mode, configured to evaluate data samples from the accelerometer during an evaluation period, the evaluation period triggered by the circuit detecting the activity signal exceeding the threshold, and the threshold adaptively adjustable based on sensor input, and the processor, based on the evaluation, configured to determine the activity level of the user, and the processor, based on the activity level, configured to determine whether to remain in the active mode or to transition to the reduced power mode.

2. The activity monitor of claim 1, wherein:
based on the activity level, the processor determines whether to remain in the active mode for the minimum period of time.

3. The activity monitor of claim 1, wherein:
the minimum period of time is based on the factors and the activity level.

4. The activity monitor of claim 1, wherein:
the evaluation period is predetermined.

5. The activity monitor of claim 1, further comprising:
an ambient light sensor providing the sensor input, wherein the processor determines whether to remain in the active mode for the minimum period of time based on an ambient light level indicated by the light sensor.

6. The activity monitor of claim 1, further comprising:
a skin temperature sensor providing the sensor input, wherein the processor determines whether to remain in the active mode for the minimum period of time based on a skin temperature of the user indicated by the skin temperature sensor.

7. The activity monitor of claim 1, wherein:
the output comprises an analog signal from the accelerometer.

8. The activity monitor of claim 1, wherein:
the activity level is determined based on at least one of amplitudes or frequencies of the data samples.

9. The activity monitor of claim 1, wherein:
the accelerometer comprises a multiple axis accelerometer, and the output is from one or more axes of the multiple axis accelerometer.

10. The activity monitor of claim 1, wherein:
a sensor sends an interrupt request to the processor to enter the active mode from the reduced power mode.

11. A method for determining activity of a user monitored by an activity monitor, comprising:
outputting signals from an accelerometer to a wake up circuit, the accelerometer adapted to be worn by the user;
determining if the signals output from the accelerometer exceed a threshold using the wake up circuit;
when the output signals exceed the threshold, evaluating data samples from the accelerometer during an evaluation period to analyze an activity level of the user using a processor, the samples from the accelerometer are not evaluated by the wake up circuit to analyze the activity level of the user; and
determining whether to continue to evaluate the samples from the accelerometer based on the activity level of the user using the processor after a minimum period of time calculated from an end of the evaluation period, such that when the output signals fail to exceed the threshold, reducing power consumption of the activity monitor by not transferring the data samples from the accelerometer to the processor.

12. The method of claim 11, further comprising:
setting the threshold based on a characteristic of the user.

13. The method of claim 11, further comprising:
setting the threshold based on previous activity of the user.

14. The method of claim 11, further comprising:
determining whether to continue to evaluate the data samples from the accelerometer based on a skin temperature of the user.

15. The method of claim 11, further comprising:
determining whether to continue to evaluate the data samples from the accelerometer based on an ambient light level.

16. The method of claim 11, further comprising:
determining whether to continue to evaluate the data samples from the accelerometer based on a time of day.

17. A non-transitory computer-readable storage apparatus having computer-readable program code embodied thereon for programming a processor to perform a method, the method comprising:
the program code configured to obtain an output signal from an accelerometer of an activity monitor adapted to be worn by a user;
the program code configured to determine if the output signal exceeds a threshold, the output signal analyzed by a wake up component of the activity monitor; and
if the output signal exceeds the threshold, the program code configured to process data samples of the accelerometer using an active mode of a processor;
the program code configured to receive sensor data from a sensor of the activity monitor adapted to be worn by the user; and
based on the processing of the data samples and the sensor data, the program code configured to determine whether to continue the active mode of the processor after a minimum period of time calculated from a start of the active mode, wherein
the threshold is adjusted based on factors representative of a type of the sensor and the activity of the user to variably trigger the active mode of the processor.

18. The computer-readable storage apparatus of claim 17, wherein:
the sensor comprises an ambient light sensor.

19. The computer-readable storage apparatus of claim 17, wherein:
the sensor comprises a skin temperature sensor.

20. The computer-readable storage apparatus of claim 17, wherein the method performed further comprises:
the program code configured to determine whether to continue the active mode of the processor based on a time of day.

21. An activity monitor, comprising:
one or more sensors, including one of the sensors as an accelerometer, outputting an activity signal, the accelerometer is adapted to be worn by a user; and
a processor comprising activity analysis logic and wake up logic,
the processor is configured to be in communication with the accelerometer,
the wake up logic determines whether the activity signal output from the accelerometer exceeds a variable threshold,
the activity analysis logic is adapted to process data samples from the accelerometer in an active mode of the processor,
the wake up logic causes the processor to enter the active mode from a reduced power mode based on whether the activity signal exceeds the variable threshold, the variable threshold being set based on variables representative of an activity level of the user and a type of the one or more sensors employed for measuring the activity level, the processor, upon entering the active mode, is configured to activate the activity analysis logic to evaluate the data samples from the accelerometer during an evaluation period, and based on the evaluation, determine the activity level of the user, and the processor, based on the activity level, is configured to determine whether to remain in the active mode or to transition to the reduced power mode.

22. The activity monitor of claim 21, further comprising:
the one or more sensors configured to provide a signal indicative of whether to enter the active mode to the processor as an input to decide whether to remain in the active mode or to transition to the reduced power mode.

23. The activity monitor of claim 22, wherein:
the one or more sensors comprise a skin temperature sensor.

24. The activity monitor of claim 22, wherein:
the one or more sensors comprise an ambient light sensor.

* * * * *